United States Patent [19]

Hassler, Jr.

[11] Patent Number: 5,540,684
[45] Date of Patent: Jul. 30, 1996

[54] METHOD AND APPARATUS FOR ELECTROSURGICALLY TREATING TISSUE

[76] Inventor: William L. Hassler, Jr., c/o Ethicon Endo-Surgery, 4545 Creek Rd., Cincinnati, Ohio 45242-2839

[21] Appl. No.: 282,522

[22] Filed: Jul. 28, 1994

[51] Int. Cl.$^6$ ................................................ A61B 17/39
[52] U.S. Cl. ........................... 606/40; 606/38; 606/51
[58] Field of Search ................................. 606/37–40, 51, 606/52

[56] References Cited

U.S. PATENT DOCUMENTS

| | | |
|---|---|---|
| 3,651,811 | 3/1972 | Hildebrandt et al. . |
| 4,232,676 | 11/1980 | Herczog . |
| 4,248,231 | 2/1981 | Herczog et al. . |
| 4,474,179 | 10/1984 | Koch . |
| 4,651,280 | 3/1987 | Chang et al. . |
| 4,658,819 | 4/1987 | Harris et al. . |
| 4,685,459 | 8/1987 | Koch et al. . |
| 4,903,696 | 2/1990 | Stasz et al. . |
| 4,938,761 | 7/1990 | Ensslin . |
| 5,057,099 | 10/1991 | Rink . |
| 5,122,137 | 6/1992 | Lennox ...................................... 606/40 |
| 5,342,357 | 8/1994 | Nardella ..................................... 606/40 |
| 5,403,312 | 4/1995 | Yates et al. ................................ 606/40 |

FOREIGN PATENT DOCUMENTS

| | | |
|---|---|---|
| 2573301 | 5/1986 | France . |
| 2455171 | 8/1976 | Germany . |
| 2213381 | 8/1989 | United Kingdom . |
| 94/10925 | 5/1994 | WIPO . |
| 95/09576 | 4/1995 | WIPO . |

*Primary Examiner*—Lee S. Cohen

[57] ABSTRACT

Tissue impedance or tissue impedance in combination with tissue temperature is used to control electrosurgical tissue treatment. Tissue impedance alone provides better control of electrosurgical treatment by determining an initial maximum tissue impedance, a minimum tissue impedance selecting a point between the maximum and minimum impedances, preferably the average, as an impedance threshold, and turning off rf power to the electrosurgical instrument when the impedance reaches the threshold as it rises from the minimum. Control may also be by the combination of tissue impedance and temperature. Temperature is controlled to maintain a selected preferred temperature and a maximum temperature is also selected so that if the tissue reaches the maximum temperature, power is turned off. Impedance control is combined with temperature control so that the temperature of the instrument is maintained at a selected preferred temperature unless a maximum temperature is exceeded, which normally will not happen. The impedance is also monitored with maximum and minimum values being determined as well as a threshold impedance between the max and the min. When the threshold, preferably the average impedance, is reached, power is removed from the instrument.

15 Claims, 7 Drawing Sheets

METHOD AND APPARATUS FOR ELECTROSURGICALLY TREATING TISSUE

BACKGROUND OF THE INVENTION

The present invention relates in general to electrosurgical treatment of tissue and, more particularly, to a method and apparatus for electrosurgical treatment wherein tissue impedance or tissue impedance in combination with tissue temperature are used to control the electrosurgical treatment.

Many available radio frequency (rf) generators for use in the medical field for surgical purposes including cauterization, dissection, transection, tissue welding and the like, generally do not effectively regulate the electrical power supplied to an electrosurgical instrument. Typically such generators control the voltage such that a selected power level is approximately delivered and a maximum power level is not exceeded. When such rf generators are used, the primary control is the experience of the surgeon who responds to what is observed as happening to the tissue being treated using the rf energy. Often, particularly for endoscopic procedures, surgeons can not see what is happening to the tissue and may not be able to react quickly enough even if good observation is possible.

A variety of instrument and rf energy generator control arrangements have been proposed. For example, temperature sensors have been incorporated into rf forceps to sense the temperatures of the contact faces of the forceps with the rf power applied to the forceps being controlled based on the temperature of one or both of the contact faces or the temperature difference between the contact faces.

Rf power has been controlled in accordance with the square of the impedance over the range of increasing tissue impedance. The differential quotient of tissue impedance has also been considered with regard to determining the initial power level and the time for switching off rf power applied to tissue.

Notwithstanding these control arrangements, there is a continuing need in the art for different approaches and techniques for the control of rf energy powered surgical instruments to better assist surgeons and improve treatment using rf energy.

SUMMARY OF THE INVENTION

This need is met by the invention of the present application wherein tissue impedance or tissue impedance in combination with tissue temperature is used to control electrosurgical tissue treatment. Tissue impedance can be used by itself for better control of electrosurgical treatment by determining an initial tissue impedance which is a maximum impedance for the tissue, a minimum impedance for the tissue which signals the end of the initial tissue heating and the onset of tissue desiccation, selecting a point between the maximum and minimum impedances as a threshold, and turning off power to the electrosurgical instrument when the impedance reaches the threshold as it rises from the minimum after falling from the maximum to the minimum. Preferably, the threshold is selected as the average between the maximum and minimum impedance values.

Further and more precise control is effected by the combination of tissue impedance and temperature to control electrosurgical treatment. The temperature is controlled to maintain a selected preferred temperature for the electrosurgical procedure being performed. A maximum temperature is also selected such that if the tissue reaches the maximum temperature the power is turned off to the electrosurgical instrument. Impedance control is combined with temperature control by incorporating the previously described impedance control of the instrument with the temperature control. Thus, the temperature of the instrument is maintained at a selected preferred temperature unless a maximum temperature is exceeded, which normally will not happen. The impedance is also monitored with maximum and minimum values being determined as well as a threshold impedance between the maximum and the minimum. When the threshold, preferably the average impedance, is reached, power is removed from the instrument.

In accordance with one aspect of the present invention, an electrosurgical apparatus for coagulating tissue during a surgical procedure comprises first and second elements electrically insulated from one another and movable relative to one another for engaging tissue to be coagulated therebetween. A power controller responsive to a power control signal provides for controlling rf energy connected to the first and second elements. Impedance measurement circuitry coupled to the first and second elements measures the impedance of tissue between the first and second elements. The impedance measuring circuitry includes a first device for storing an initial impedance value which is a maximum impedance, and a second device for storing a minimum impedance value. A threshold determining circuit is coupled to the first and second devices for determining a threshold impedance value between the initial maximum impedance value and the minimum impedance value. A first comparator compares measured impedance values to the threshold impedance value and generates a power control signal to stop the power controller upon the measured impedance value exceeding the threshold impedance value.

For use of commonly available rf power generators, the power controller includes at least one electrical switch for selectively applying rf energy to the first and second elements for coagulating tissue positioned between the first and second elements. The threshold determining circuit comprises an averaging circuit for determining an average impedance value approximately midway between the initial maximum impedance value and the minimum impedance value and setting the threshold impedance to the average impedance value.

The electrosurgical apparatus may further comprise at least one temperature sensor coupled to the first element or at least one temperature sensor coupled to the first element and at least one temperature sensor coupled to the second element. A third device determines a maximum acceptable temperature for coagulating tissue. A second comparator compares the maximum acceptable temperature to a tissue temperature. The tissue temperature is derived from temperatures indicated by the at least one temperature sensor coupled to the first element or the temperature sensors coupled to the first and second elements. The second comparator generates a control signal to enable the power controller as long as the tissue temperature does not exceed the maximum acceptable temperature and to disable the power controller upon a tissue temperature exceeding the maximum acceptable temperature.

In accordance with another aspect of the present invention, an apparatus for electrosurgically treating tissue during a surgical procedure comprises an instrument for applying rf energy to tissue to be electrosurgically treated. Impedance measurement circuitry is coupled to the instrument for measuring the impedance of tissue engaged by the instrument and for generating a representative impedance signal. Temperature measurement circuitry is coupled to the instrument for measuring the temperature of tissue engaged by the instrument and for generating a representative temperature signal. Control circuitry responsive to the impedance signal and the temperature signal is provided for controlling rf energy connected to the instrument.

In one embodiment of the invention, the instrument comprises a pair of forceps for coagulating tissue during a surgical procedure. The impedance measurement circuitry comprises a first device for storing an initial maximum impedance value and a second device for storing a minimum impedance value. The control circuitry comprises a threshold determining circuit connected to the first and second devices for determining a threshold impedance value between the initial maximum impedance value and the minimum impedance value. A first comparator compares measured impedance values to the threshold impedance value and generates a control signal to stop the power controller upon the measured impedance value exceeding the threshold impedance value. For use of commonly available rf power generators, the control circuitry includes at least one electrical switch for selectively applying rf energy to the instrument.

In accordance with still another aspect of the present invention, a method of operating apparatus for electrosurgically treating tissue during a surgical procedure comprises the steps of: applying rf energy to tissue to be electrosurgically treated by means of an electrosurgical instrument; measuring the impedance of tissue engaged by the electrosurgical instrument; generating an impedance signal representative of the impedance of the tissue; measuring the temperature of tissue engaged by the electrosurgical instrument; generating a temperature signal representative of the temperature of the tissue; and, controlling the rf energy applied to the electrosurgical instrument in response to the impedance signal and the temperature signal.

The step of controlling the rf energy applied to the electrosurgical instrument may comprise the steps of: storing an initial maximum impedance value; storing a minimum impedance value; determining a threshold impedance value between the initial maximum impedance value and the minimum impedance value; comparing measured impedance values to the threshold impedance value; and, generating a control signal to stop the power controller upon the measured impedance value exceeding the threshold impedance value.

The step of applying rf energy to tissue to be electrosurgically treated by means of an electrosurgical instrument may comprise the step of selectively applying rf energy to the electrosurgical instrument.

The step of controlling the rf energy applied to the electrosurgical instrument may also comprise the steps of: storing a maximum acceptable temperature for operation of the electrosurgical instrument; comparing temperature signals and the maximum acceptable temperature; enabling the step of applying rf energy as long as temperature signals do not exceed the maximum acceptable temperature; and, disabling the step of applying rf energy for a temperature signal exceeding the maximum acceptable temperature.

In accordance with yet another aspect of the present invention, a method of operating electrosurgical apparatus for coagulating tissue during a surgical procedure comprises the steps of: engaging tissue to be coagulated between first and second elements electrically insulated from one another and movable relative to one another; selectively controlling rf energy connected to the first and second elements for coagulating tissue positioned therebetween; measuring the impedance of tissue positioned between the first and second elements; storing an initial maximum impedance value; storing a minimum impedance value; determining a threshold impedance value between the initial maximum impedance value and the minimum impedance value; comparing measured impedance values to the threshold impedance value; and, stopping the rf energy connected to the first and second elements upon the measured impedance value exceeding the threshold impedance value.

The step of selectively controlling rf energy connected to the first and second elements comprises the step of switching the rf energy on and off.

The step of determining a threshold impedance value between the initial maximum impedance value and the minimum impedance value may comprise the steps of: determining an average impedance value between the initial maximum impedance value and the minimum impedance value; and, setting the threshold impedance to the average impedance value.

The method may further comprise the steps of: coupling temperature sensors to the first and second elements; storing a maximum acceptable temperature for coagulating tissue; comparing temperatures from the temperature sensors and the maximum acceptable temperature; enabling the rf energy as long as a temperature of one of the temperature sensors does not exceed the maximum acceptable temperature; and, disabling the rf energy upon a temperature of one of the temperature sensors exceeding the maximum acceptable temperature.

In accordance with still yet another aspect of the present invention, a method of operating apparatus for electrosurgically treating tissue during a surgical procedure comprises the steps of: applying rf energy to tissue to be electrosurgically treated by means of an electrosurgical instrument through an rf energy switch; measuring the temperature of tissue engaged by the electrosurgical instrument; generating a temperature signal representative of the temperature of the tissue; controlling the rf energy switch in response to the temperature signal to maintain a selected temperature for tissue engaged by the electrosurgical instrument; measuring the impedance of tissue engaged by the electrosurgical instrument; generating an impedance signal representative of the impedance of the tissue; and, controlling the rf energy switch in response to the impedance signal to stop the application of the rf energy to tissue engaged by the electrosurgical instrument.

The step of controlling the rf energy switch in response to the impedance signal to stop the application of the rf energy to tissue engaged by the electrosurgical instrument may comprise the steps of: storing an initial maximum impedance value; storing a minimum impedance value; determining a threshold impedance value between the initial maximum impedance value and the minimum impedance value; comparing measured impedance values to the threshold impedance value; and, generating a control signal to stop the power controller upon the measured impedance value exceeding the threshold impedance value.

The step of determining a threshold impedance value between the initial maximum impedance value and the minimum impedance value may comprise finding the midpoint between the initial maximum impedance value and the minimum impedance value.

The method may further comprise the steps of: setting a maximum temperature of tissue engaged by the electrosurgical instrument; comparing measured temperature values to the maximum temperature; and, generating a control signal to stop the power controller upon a measured temperature value exceeding the maximum temperature value.

It is thus an object of the present invention to provide an improved method and apparatus for controlling electrosurgical instrument control; to provide an improved method and apparatus for controlling electrosurgical instrument control wherein an impedance threshold between an initial maximum impedance and a minimum impedance is selected and used to shut off rf power to the instrument when the threshold is reached; and, to provide an improved method and apparatus for controlling electrosurgical instrument control wherein both temperature and impedance measurements are used to control the instrument.

Other objects and advantages of the invention will be apparent from the following description, the accompanying drawings and the appended claims.

BRIEF DESCRIPTION OF THE INVENTION

Figure 3:
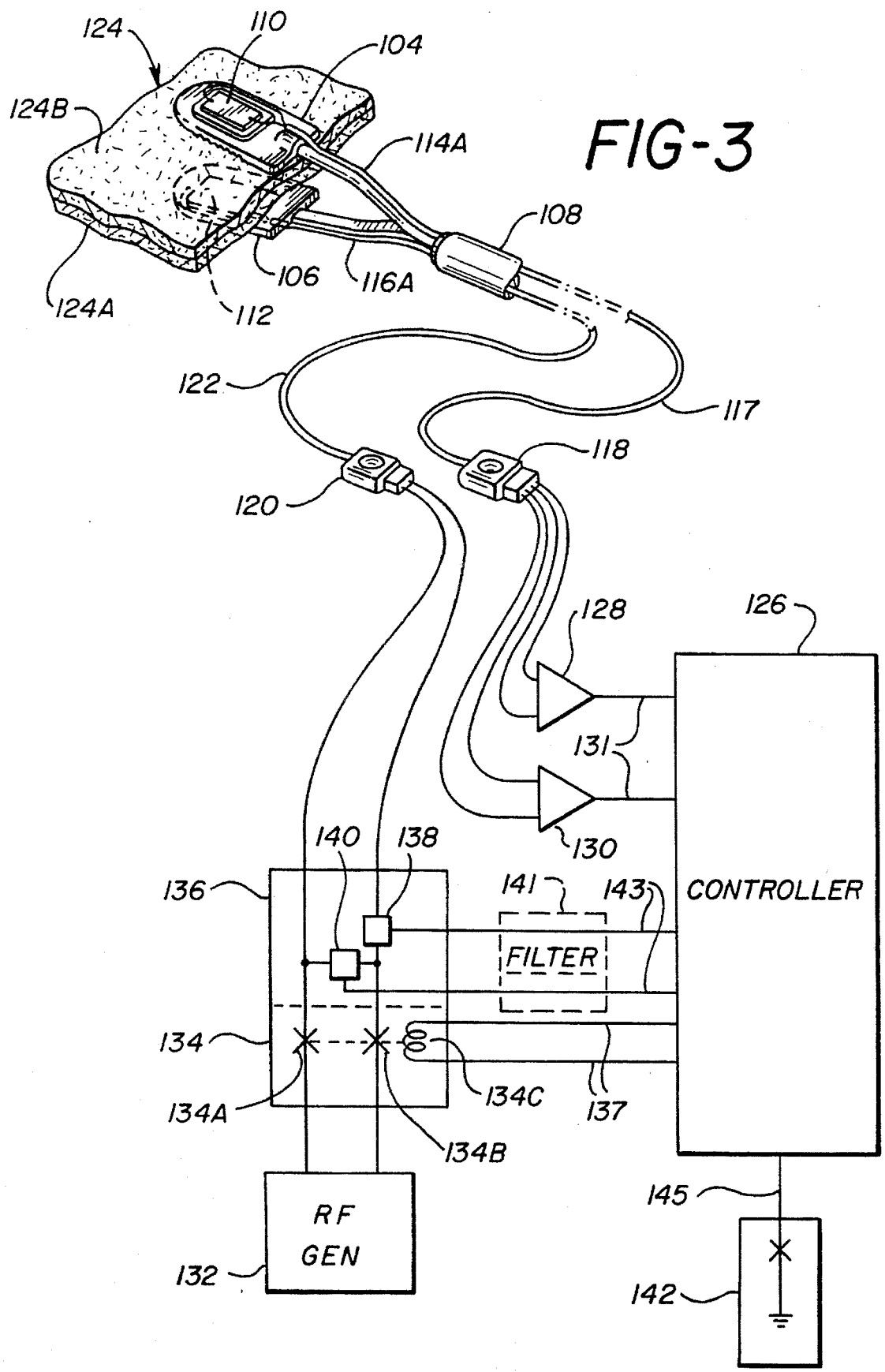
FIG. 3 is a schematic block diagram of apparatus for controlling the forceps of FIG. 1 for electrosurgically treating tissue in accordance with the present invention.
Figure 4:
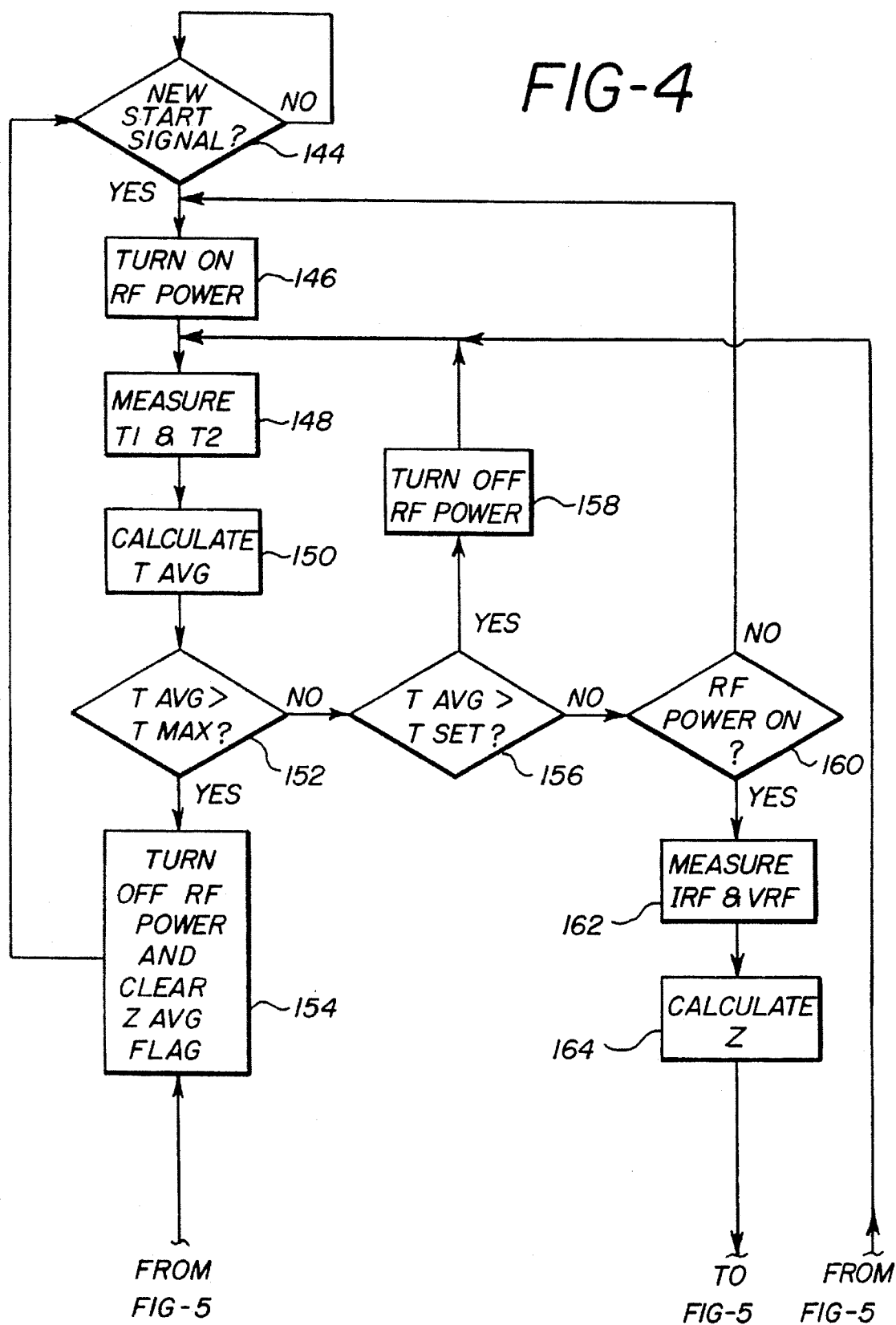
Figure 5:
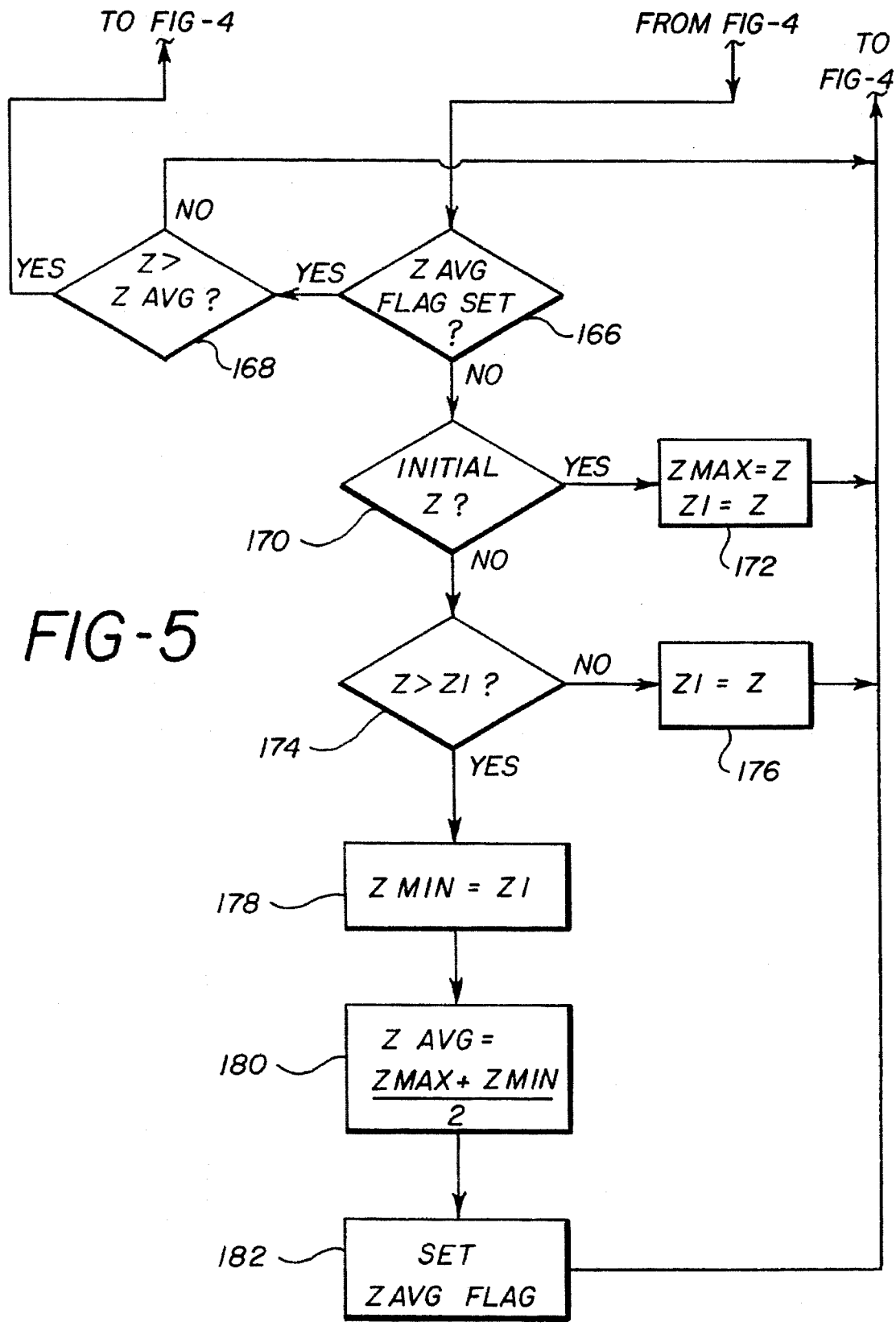
Figure 6:
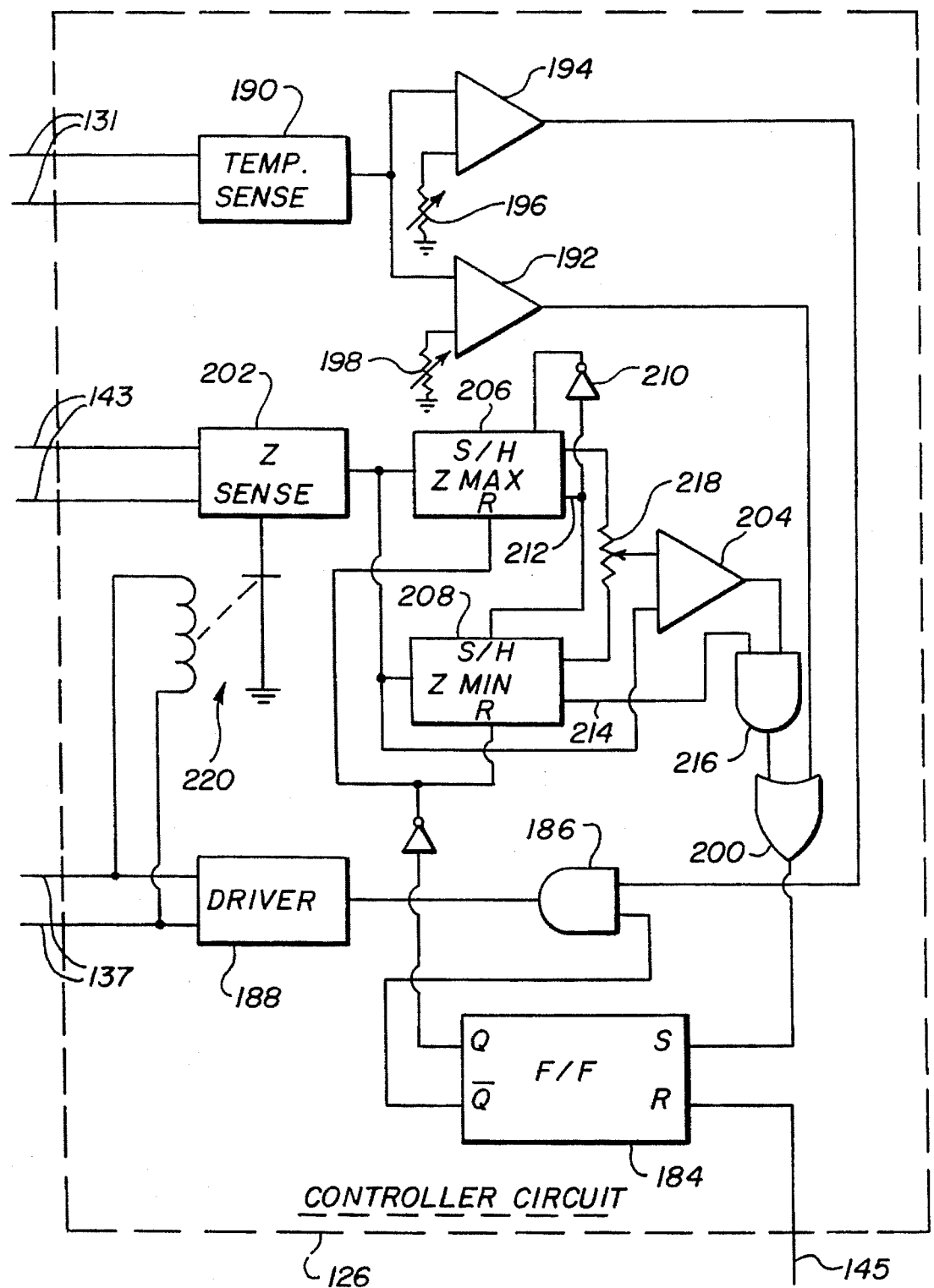
Figure 7:
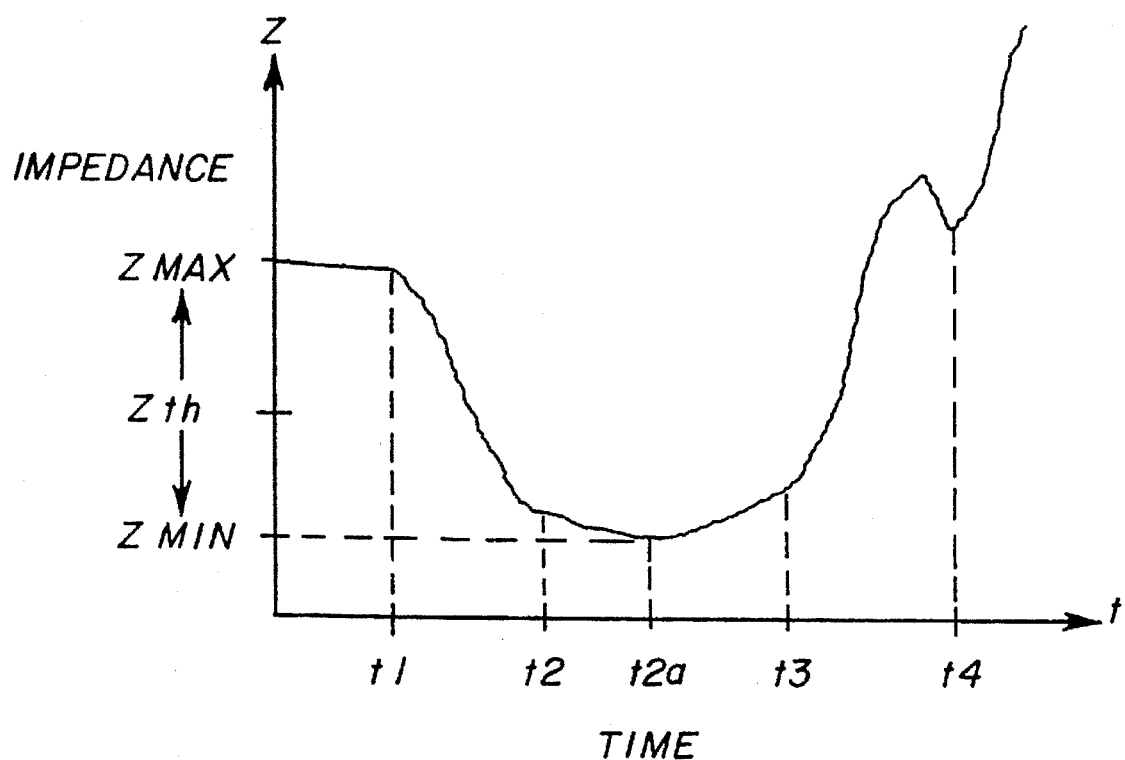

FIGS. 4 and 5 form a flow chart for operation of a microprocessor controller when used in the apparatus of FIG. 3;

FIG. 6 is a schematic block diagram of an alternate embodiment of a controller for use in the apparatus of FIG. 3; and FIG. 7 is a graph illustrating the change of impedance over time during application of electrosurgical energy to tissue.

DETAILED DESCRIPTION OF THE INVENTION

Figure 1:
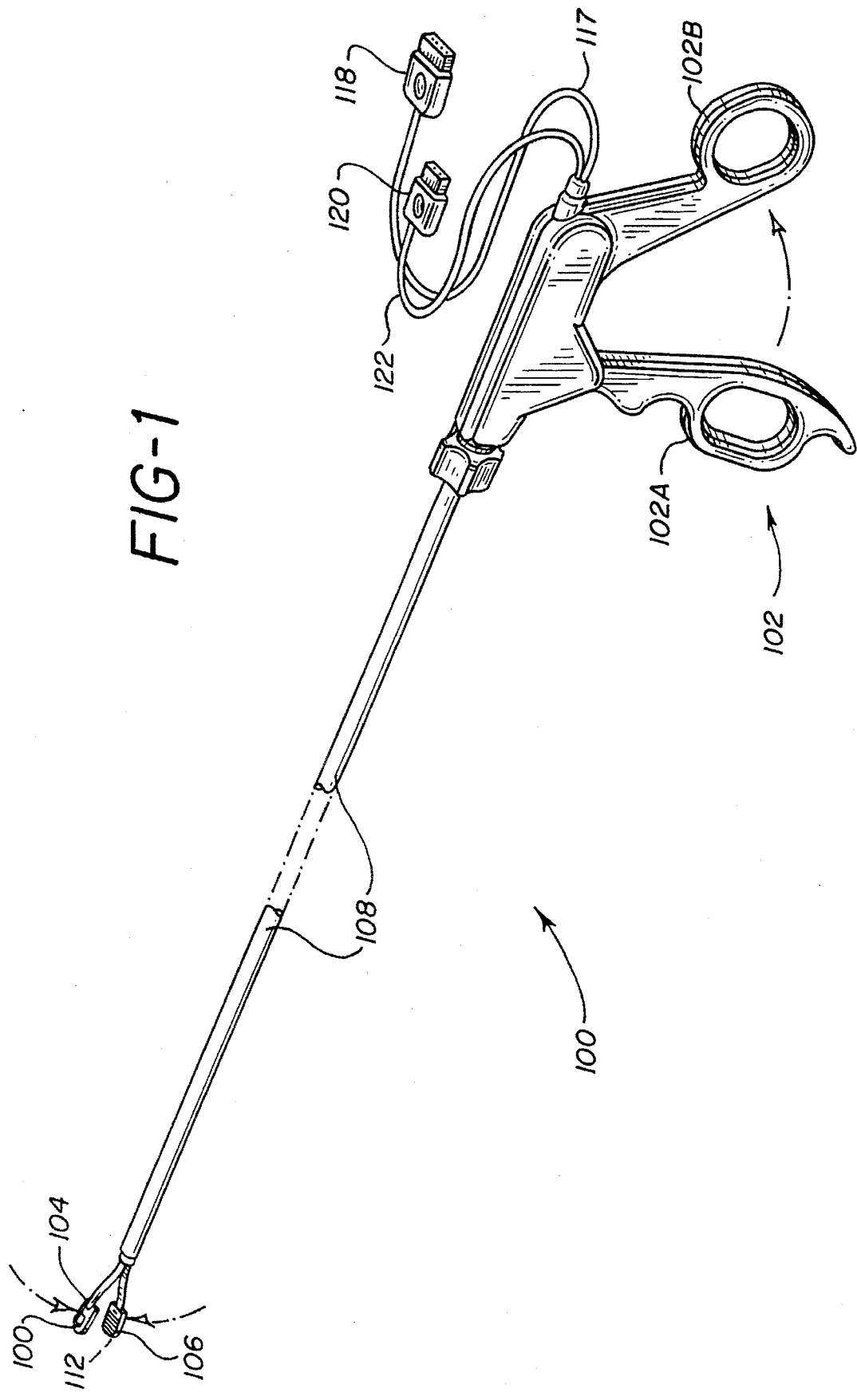
FIG. 1 is a perspective view of a pair of endoscopic bipolar electrosurgical forceps operable in accordance with the present invention.

While the present invention is generally applicable to a variety of surgical instruments, both conventional and endoscopic, it will be described herein with reference to a pair of endoscopic bipolar electrosurgical forceps for which the invention is initially being applied. As shown in FIG. 1, a pair of endoscopic bipolar electrosurgical forceps 100 operable in accordance with the present invention includes a proximal handle operating end 102 and first and second gripping elements 104, 106 at the distal end of the instrument. The gripping elements are electrically insulated from one another and movable relative to one another for engaging tissue to be coagulated therebetween.

The distal gripping elements 104, 106 are separated from the proximal handle operating end 102 by a long tubular member 108. In terms of gripping tissue, the pair of endoscopic bipolar electrosurgical forceps 100 are operated in a conventional well known manner by moving the forward handle portion 102A toward the rearward handle portion 102B. Accordingly, description of the forceps will be made only to the extent necessary for understanding the present invention.

Figure 2:
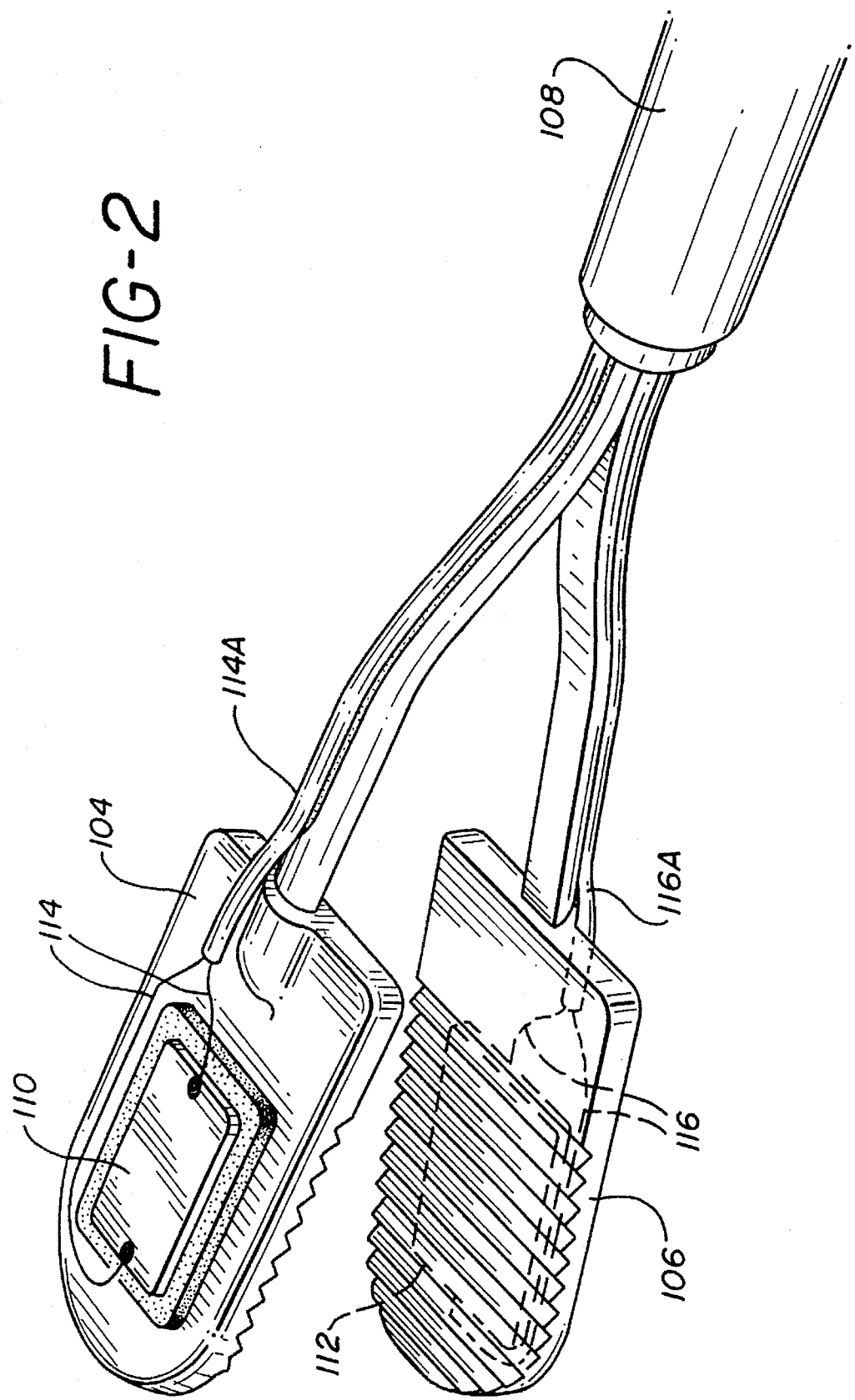
FIG. 2 is a perspective view of tissue gripping elements of the forceps of FIG. 1 shown on an enlarged scale to illustrate temperature sensors coupled to the tissue gripping elements.

For operation in accordance with the present invention, the gripping elements 104, 106 are modified to couple at least one temperature sensor to each of the gripping elements 104, 106. In the illustrated embodiment, a single resistive thermal device (RTD) 110 is coupled to the gripping element 104 and a single RTD 112 is coupled to the gripping element 106, see FIG. 2. While RTD's secured to the outer back surfaces of the gripping elements 104, 106, are utilized in the illustrated embodiment, it should be apparent that other temperature sensors can be coupled to the gripping elements 104, 106 in a variety of ways, for example by embedding the sensors in the gripping elements 104, 106.

Two pairs of electrical conductors 114, 116 are provided for making electrical connections to the RTD's 110, 112. The electrical conductors are housed in sheaths 114A, 116A which are routed through the long tubular member 108 and ultimately joined in a conductor protective sheath 117 which terminates in a four conductor connector 118 shown in FIG. 1 for connection to temperature monitoring circuitry. A second two conductor connector 120 secured to the end of conductor protective sheath 122 provides for connection of radio frequency (rf) energy to the gripping members 104, 106 to perform electrosurgical treatment using the endoscopic bipolar electrosurgical forceps 100. Connection of these elements for operation of the present invention will now be described with reference to FIGS. 3–6.

FIG. 3 is a schematic block diagram of apparatus for controlling the pair of endoscopic bipolar electrosurgical forceps of FIG. 1 for electrosurgically treating tissue in accordance with the present invention. The same identification numerals are used for corresponding elements from other drawings within the application. In FIG. 3, a section of tissue 124 comprising two layers of tissue 124A and 124B which are to be engaged by the gripping elements 104, 106 and electrosurgically treated thereby are shown inserted between the gripping elements 104, 106. In the case of the pair of endoscopic bipolar electrosurgical forceps 100, the two layers of tissue 124A, 124B are to be welded together.

Since tissue welding is not very well understood in the art at the present time, tissue welding is defined herein as bringing two pieces of tissue together and joining them together. The welding operation is believed to be performed by causing collagen molecules in the tissue to be mobilized by severing the disulfide cross linkages. The collagen molecules then diffuse across the interface between the two pieces of tissue. Finally, new disulfide linkages are formed across the interface between the two pieces of tissue thereby causing the interface to disappear.

While temperature and impedance have been used separately to control electrosurgical instruments, the two can be advantageously combined to provide an optimum control of such instruments. Tissue temperature defines the level of activation energy available for the chemical reaction noted above for tissue welding; and, the impedance defines the rate at which the reaction takes place. By utilizing both tissue temperature and impedance, optimum control can be attained as will be described.

FIG. 7 graphically illustrates the change of impedance over time during application of electrosurgical energy to tissue. In FIG. 7, the onset of electrosurgical energy to the tissue occurs at time t1. Time t2 is believed to correspond to the end of the tissue heating phase and beginning of tissue desiccation. It is further believed that tissue desiccation is almost completed by time t3, and that tissue carbonization begins at time t4.

While optimum control is attained by utilizing both tissue temperature and impedance as will be described, the present invention also provides improved control of an electrosurgical instrument by means of impedance measurement alone. In accordance with this aspect of the present invention an initial tissue impedance, a maximum impedance for the tissue, Zmax, is determined (for example at time t1). A minimum impedance for the tissue, Zmin, which is believed to signal the approximate end of the initial tissue heating and the onset of tissue desiccation, is determined (for example at time t2a). An impedance between the maximum and minimum impedances, Zth, is selected as a threshold, and rf power to the electrosurgical instrument is turned off when the impedance reaches the threshold as it rises from the minimum. Preferably, the threshold is selected as the average between the maximum and minimum impedance values. This impedance control arrangement will be further described with reference to the combined tissue impedance temperature control.

As shown in FIG. 3, the RTD's 110, 112 are connected to a controller circuit 126 through preprocessing amplifiers represented by a pair of amplifiers 128, 130. The output signals from the amplifiers 128, 130 are passed to the controller circuit 126 via conductors 131. The output signals from the amplifiers 128, 130 are representative of the temperatures of the gripping elements 104, 106 and, accordingly, the temperature of the section of tissue 124 gripped between the gripping elements such that the controller circuit 126 can monitor the temperatures of the gripping elements 104, 106 and thereby the temperature of the section of tissue 124.

An rf generator 132 provides rf energy to the gripping elements 104, 106 through a power controller 134, impedance measurement circuitry 136 and the connector 120. The power controller 134 is responsive to a power control signal generated by the controller circuit 126 for controlling rf energy connected to the gripping elements 104, 106. The impedance measurement circuitry 136 is coupled to the gripping elements 104, 106 for measuring the impedance of the tissue 124 gripped therebetween.

In the illustrative embodiment of FIG. 3, the power controller 134 comprises a pair of normally open relay contacts 134A and 134B (indicated by an X) which are opened and closed by an associated relay coil 134C which receives control signals over conductors 137. Of course, other electromechanical and solid state switching devices can be used in the invention of the present application.

The impedance measurement circuitry 136 comprises a low impedance current monitoring device 138 connected in series with the rf generator 132; and, a high impedance voltage monitoring device 140 connected in parallel across the rf generator 132. A noise filter 141 may also be inserted between the current and voltage monitoring devices 138, 140 and the controller circuit 126 to filter noise out of the signals generated by the current and voltage monitoring devices 138, 140 which are past to the controller circuit 126 over conductors 143.

In a working embodiment of the present invention, current and voltage monitoring transformers were used for the current and voltage monitoring devices 138, 140. The current monitoring transformer was constructed on a toroidal iron ferrite core manufactured by Micrometals and having a one inch outer diameter. The current monitoring transformer was wound with 2 primary turns and 25 secondary turns, both primary and secondary being 24 gauge wire. The voltage monitoring transformer was constructed using the same type core and 24 gauge wire but was wound with 32 primary windings and 2 secondary windings. Of course, other current and voltage monitoring devices can be used in the invention of the present application. In any event, current and voltage signals representative of the rf current flowing through the section of tissue 124 and the rf voltage connected across the section of tissue 124 are passed to the controller circuit 126 which converts the current and voltage signals tissue impedance values.

A start switch 142 is connected to the controller circuit 126 via a conductor 145 to generate a start signal to thereby initiate application of rf energy or power to the gripping elements 104, 106. The rf power is then controlled in accordance with the present invention such that consistent tissue welding is performed using the pair of endoscopic bipolar electrosurgical forceps 100. In particular, in the illustrated embodiment, the temperature and impedance of the section of tissue 124 are monitored and the temperature maintained at a selected temperature until either an impedance threshold is exceeded or, in the event of some problem, a maximum temperature is exceeded at which time the rf power is removed until the start switch 142 is once again operated. The start switch 142 should not be operated again until the surgeon controlling the pair of endoscopic bipolar electrosurgical forceps 100 has repositioned the forceps and is ready to electrosurgically treat the tissue which has then been engaged.

The controller circuit 126 can take the form of a processor, such as a microprocessor, in which case, the processor may be programmed to operate in accordance with the flow chart shown in FIGS. 4 and 5. Alternately, the controller circuit 126 can be a dedicated circuit for example as shown in FIG. 6. Operation of a processor controlled system will now be described with reference to FIGS. 4 and 5.

Initially referring to FIG. 4, once the system has been activated, the processor will search for a new start signal as generated by activation of the start switch 142, see block 144. Upon receipt of a start signal from the start switch 142, the coil 134c is activated to turn on rf power to the pair of endoscopic bipolar electrosurgical forceps 100, see block 146.

The temperatures, T1 and T2, of the gripping elements 104, 106, respectively, are taken and an average temperature TAVG is calculated as being representative of the temperature of the section of tissue 124, see blocks 148, 150. Of course, the temperatures T1 and T2 could be individually utilized if desired.

A maximum temperature TMAX is selected which should never be reached in a properly operating system. Above TMAX, rf power is removed from the gripping elements 104, 106 until the next operation of the start switch 142. While TMAX should never be reached during proper operation of the system, it serves as a safety valve to ensure removal of rf power in the event of a problem. TMAX may be set for example between 85° C. and 100° C. In any event, TAVG is compared to TMAX: if TAVG is greater than TMAX, the rf power is turned off by deactivating the coil 134C, a flag indicating the determination of ZAVG is cleared and the processor returns to the block 144 to search for a new start signal as generated by activation of the start switch 142, see blocks 152, 154, the determination of ZAVG and corresponding flag will be described with reference to FIG. 5; if TAVG is not greater than TMAX, TAVG is compared to TSET, a desired operating temperature for the gripping elements 104, 106, see blocks 152, 156.

If TAVG is greater than TSET, the rf power is turned off by deactivating the coil 134C, see blocks 156, 158. This enters the temperature control loop including blocks 148, 150, 152, 156 and 158. The processor continues to loop, provided TAVG does not exceed TMAX, which it should not since rf power has been removed from the gripping elements 104, 106, until TAVG is not greater than TSET. At this point, the processor determines whether rf power is on or not, see block 160. If the rf power is not on, it is turned on by returning to the block 146. If rf power is turned on, the rf current IRF and rf voltage VRF are measured by reading the output signals from the current and voltage monitoring devices 138, 140 and the impedance Z is calculated, see blocks 162, 164.

Referring now to FIG. 5, the flag indicating the determination of ZAVG is checked, see block 166. If the flag is set indicating that ZAVG has been determined, the calculated impedance Z is compared to ZAVG, see block 168. If Z is greater than or equal to ZAVG, the rf power is turned off by deactivating the coil 134C, the flag indicating the determination of ZAVG is cleared and the processor returns to the block 144 to search for a new start signal as generated by activation of the start switch 142, see blocks 168, 154. If Z is less than ZAVG, the processor returns to the block 148 to measure T1 and T2 and continues in the flow chart.

If the flag indicating that ZAVG has been determined is not set, the processor determines whether Z is the initial and hence maximum Z value, see FIG. 7 and related description, see block 170. If Z is the initial Z, ZMAX is set equal to Z and a variable Z1 is also set equal to Z. The processor then returns to the block 148 to measure T1 and T2 and continues in the flow chart, see block 172. If Z is not the initial Z, then Z is compared to Z1, see block 174. If Z is not greater than Z1, then Z1 is set equal to Z and the processor then returns to the block 148 to measure T1 and T2 and continues in the flow chart, see block 176.

If Z is greater than Z1, then ZMIN is set equal to Z1 and ZAVG is calculated by dividing ZMAX+ZMIN by 2, see blocks 178, 180. The ZAVG flag is then set and the processor then returns to the block 148 to measure T1 and T2 and continues in the flow chart, see block 182. Accordingly, the temperature is controlled to substantially equal TSET and the rf power is turned off until a new start signal is received if either: the calculated impedance Z exceeds ZAVG; or, if the calculated average temperature TAVG exceeds TMAX.

An example of the controller circuit 126 configured as a dedicated circuit will now be described with reference to an illustrative embodiment of such a circuit shown in FIG. 6 as a schematic block diagram. The new start signal as generated by activation of the start switch 142 is received on a reset input of a set/reset flip-flop 184. Resetting the flip-flop circuit 184 enables an AND gate 186 whose output is connected to a driver circuit 188. The output signals from the amplifiers 128, 130 representative of the temperature of the gripping elements 104, 106 are passed to a temperature sense circuit 190 of the controller circuit 126 via conductors 131.

The temperature sense circuit 190 generates an output signal representative of the temperature of the section of tissue 124, for example the average of the temperatures of the gripping elements 104, 106. The output signal from the temperature sense circuit 190 is passed to two comparator circuits 192, 194. The comparator circuit 194 compares the output signal from the temperature sense circuit 190 to TSET which is set by a potentiometer 196 with the output signal from the comparator 194 being passed to the AND gate 186.

Thus, when the AND gate 186 is enabled by the flip-flop circuit 184, the comparator 194 controls the driver circuit 188 to apply rf power to the gripping elements 104, 106 whenever the sensed temperature is less than or equal to TSET. Whenever the sensed temperature is greater than TSEt, the comparator 194 controls the driver circuit 188 to disconnect rf power from the gripping elements 104, 106. In this way, the temperature of the gripping elements 104, 106 and the section of tissue 124 are maintained at substantially the temperature TSET.

The comparator 192 compares the output signal from the temperature sense circuit 190 to TMAX which is set by a potentiometer 198 with the output signal from the comparator 192 being passed to an OR gate 200. The output of the OR gate is connected to the set input of the flip-flop 184 such that if TMAX is exceeded, the flip-flop 184 is set disabling the AND gate 186.

Current and voltage signals on the conductors 143 are passed to an impedance sense circuit 202 which continuously calculates a corresponding impedance Z signal which is passed to a comparator 204, a ZMAX sample-and-hold, S/H, circuit 206 and a ZMIN sample-and-hold, S/H, circuit 208.

The ZMAX S/H circuit 206 is initially enabled through an inverter 210 which is connected to an output 212 of the circuit 206 indicating that it is not yet holding a ZMAX value. Since the initial impedance value measured will be a maximum, this value will be captured and retained by the ZMAX S/H circuit 206. At this time, the output 212 changes to disable the ZMAX S/H circuit 206 and enable the ZMIN circuit 208.

The ZMIN S/H circuit 208 will be enabled until it has captured and retains the ZMIN value at which time the impedance signals from the impedance sense circuit 202 will rise such that there will be no more changes in the ZMIN S/H circuit output. An output 214 of the ZMIN S/H circuit 208 is connected to an AND gate 216 such that the AND gate 216 is enabled when ZMIN has been determined.

A potentiometer 218 is connected between the outputs of the ZMAX and ZMIN S/H circuits 206, 208 with a wiper of the potentiometer being connected as an input to the comparator 204. Accordingly, by adjusting the potentiometer 218, a value between ZMAX and ZMIN can be selected as a threshold value. For example, a middle value can be selected such that the threshold value would be approximately the average between ZMAX and ZMIN. Of course other threshold values can be selected as required.

When the impedance Z signal from the impedance sense circuit 202 exceeds the threshold value determined by the potentiometer 218, the output of the comparator 204 is passed through the AND gate 216 and the OR gate 200 to set the flip-flop circuit 184 which resets the ZMAX and ZMIN S/H circuits 206, 208 for the next operation of the controller circuit 126 and controls the driver circuit 188 to disconnect rf power from the gripping elements 104, 106. It is noted that a normally closed contact (indicated by a dash) of a relay 220 is also controlled by the driver circuit 188 to lock-up the output of the impedance Z signal from the impedance sense circuit 202 whenever the rf power is not connected to the gripping elements 104, 106. Otherwise, erroneous impedance signals would be generated by the impedance sense circuit 202.

Having thus described the invention of the present application in detail and by reference to preferred embodiments thereof, it will be apparent that modifications and variations are possible without departing from the scope of the invention defined in the appended claims.

What is claimed is:

1. An electrosurgical apparatus for coagulating tissue during a surgical procedure, said apparatus comprising:

first and second elements electrically insulated from one another and movable relative to one another for engaging tissue to be coagulated therebetween;

a power controller responsive to a power control signal for controlling RF energy connected to said first and second elements;

impedance measurement circuitry coupled to said first and second elements for measuring the impedance of tissue between said first and second elements, said impedance measuring circuitry including:

a first device for storing an initial maximum impedance value; and a second device for storing a minimum impedance value;

a threshold determining circuit coupled to said first and second devices for determining a threshold impedance value between said initial maximum impedance value and said minimum impedance value; and a first comparator operatively associated with said threshold determining circuit for comparing measured impedance values to said threshold impedance value and generating a power control signal to stop said power controller upon said measured impedance value exceeding said threshold impedance value.

2. An electrosurgical apparatus for coagulating tissue during a surgical procedure as claimed in claim 1 wherein said power controller includes at least one electrical switch for selectively applying rf energy to said first and second elements for coagulating tissue positioned between said first and second elements.

3. An electrosurgical apparatus for coagulating tissue during a surgical procedure as claimed in claim 1 wherein said threshold determining circuit comprises an averaging circuit for determining an average impedance value approximately midway between said initial maximum impedance value and said minimum impedance value and setting said threshold impedance to said average impedance value.

4. An electrosurgical apparatus for coagulating tissue during a surgical procedure as claimed in claim 1 further comprising:

at least one temperature sensor coupled to said first element;

a third device for determining a maximum acceptable temperature for coagulating tissue; and a second comparator operatively associated with said third device for comparing said maximum acceptable temperature to a tissue temperature derived from temperatures indicated by said at least one temperature sensor coupled to said first element and generating a control signal to enable said power controller as long as said tissue temperature does not exceed said maximum acceptable temperature and to disable said power controller upon a tissue temperature exceeding said maximum acceptable temperature.

5. An electrosurgical apparatus for coagulating tissue during a surgical procedure as claimed in claim 4 further comprising at least one temperature sensor coupled to said second element and wherein said tissue temperature is derived from temperatures indicated by said at least one temperature sensor coupled to said first element and said at least one temperature sensor coupled to said second element.

6. A method of operating electrosurgical apparatus for coagulating tissue during a surgical procedure, said method comprising the steps of:

engaging tissue to be coagulated between first and second elements electrically insulated from one another and movable relative to one another;

selectively controlling RF energy connected to said first and second elements for coagulating tissue positioned therebetween;

measuring the impedance of tissue positioned between said first and second elements;

storing an initial maximum impedance value;

storing a minimum impedance value;

determining a threshold impedance value between said initial maximum impedance value and said minimum impedance value;

comparing a measured impedance value to said threshold impedance value; and stopping said RF energy connected to said first and second elements upon said measured impedance value exceeding said threshold impedance value.

7. A method of operating electrosurgical apparatus for coagulating tissue during a surgical procedure as claimed in claim 6 wherein said step of selectively controlling rf energy connected to said first and second elements comprises the step of switching said rf energy on and off.

8. A method of operating electrosurgical apparatus for coagulating tissue during a surgical procedure as claimed in claim 6 wherein the step of determining a threshold impedance value between said initial maximum impedance value and said minimum impedance value comprises the steps of:

determining an average impedance value between said initial maximum impedance value and said minimum impedance value; and setting said threshold impedance value to said average impedance value.

9. A method of operating electrosurgical apparatus for coagulating tissue during a surgical procedure as claimed in claim 6 further comprising the steps of:

coupling at least one temperature sensor to said first element;

determining a maximum acceptable temperature;

comparing temperatures from said temperature sensor and said maximum acceptable temperature;

enabling said RF energy as long as a temperature of said temperature sensor does not exceed said maximum acceptable temperature; and disabling said RF energy upon a temperature of said temperature sensor exceeding said maximum acceptable temperature.

10. A method of operating electrosurgical apparatus for coagulating tissue during a surgical procedure as claimed in claim 6 further comprising the steps of:

coupling at least one temperature sensor to said first and second elements;

storing a maximum acceptable temperature for coagulating tissue;

comparing temperatures from at least one of said temperature sensors and said maximum acceptable temperature;

enabling said rf energy as long as a temperature of one of said temperature sensors does not exceed said maximum acceptable temperature; and disabling said rf energy upon a temperature of one of said temperature sensors exceeding said maximum acceptable temperature.

11. An apparatus for electrosurgically treating tissue during a surgical procedure, said apparatus comprising:

an instrument for applying RF energy to tissue to be electrosurgically treated;

impedance measurement circuitry coupled to said instrument for measuring the impedance of tissue engaged by said instrument and for generating a representative impedance signal wherein said impedance measurement circuitry comprises:
  a first device for storing an initial maximum impedance value; and
  a second device for storing a minimum impedance value;
temperature measurement circuitry coupled to said instrument for measuring the temperature of tissue engaged by said instrument and for generating a representative temperature signal; and
control circuitry operatively associated with said impedance circuitry and said temperature measurement circuitry and responsive to said impedance signal and said temperature signal for controlling RF energy connected to said instrument, wherein said control circuitry comprises:
  a threshold determining circuit connected to said first and second devices for determining a threshold impedance value between said initial maximum impedance value and said minimum impedance value; and
  a first comparator operatively associated with said threshold determining circuit for comparing a measured impedance value to said threshold impedance value and generating a control signal upon said measured impedance value exceeding said threshold impedance value.

12. A method of operating apparatus for electrosurgically treating tissue during a surgical procedure, said method comprising the steps of:
  applying RF energy to tissue to be electrosurgically treated by means of an electrosurgical instrument;
  measuring the impedance of tissue engaged by said electrosurgical instrument;
  generating an impedance signal representative of the impedance of said tissue;
  measuring the temperature of tissue engaged by said electrosurgical instrument;
  generating a temperature signal representative of the temperature of said tissue; and
  controlling the RF energy applied to said electrosurgical instrument in response to said impedance signal and said temperature signal wherein said step of controlling the RF energy applied to said electrosurgical instrument comprises the steps of:
  storing an initial maximum impedance value;
  storing a minimum impedance value;
  determining a threshold impedance value between said initial maximum impedance value and said minimum impedance value;
  comparing a measured impedance value to said threshold impedance value; and
  generating a control signal upon said measured impedance value exceeding said threshold impedance value.

13. A method of operating apparatus for electrosurgically treating tissue during a surgical procedure as claimed in claim 12 wherein the step of determining a threshold impedance value between said initial maximum impedance value and said minimum impedance value comprises finding the midpoint between said initial maximum impedance value and said minimum impedance value.

14. A method of operating apparatus for electrosurgically treating tissue during a surgical procedure as claimed in claim 26 further comprising the steps of:
  setting a maximum temperature of tissue engaged by said electrosurgical instrument;
  comparing measured temperature values to said maximum temperature; and
  generating a control signal upon a measured temperature value exceeding said maximum temperature value.

15. A method of operating apparatus for electrosurgically treating tissue during a surgical procedure, said method comprising the steps of:
  applying RF energy to tissue to be electrosurgically treated by means of an electrosurgical instrument through an RF energy switch;
  measuring the temperature of tissue engaged by said electrosurgical instrument;
  generating a temperature signal representative of the temperature of said tissue;
  controlling said RF energy switch in response to said temperature signal to maintain a selected temperature for tissue engaged by said electrosurgical instrument;
  measuring the impedance of tissue engaged by said electrosurgical instrument;
  generating an impedance signal representative of the impedance of said tissue; and
  controlling the RF energy switch in response to said impedance signal to stop the application of said RF energy to tissue engaged by said electrosurgical instrument wherein said step of controlling the RF energy switch in response to said impedance signal to stop the application of said RF energy to tissue engaged by said electrosurgical instrument comprises the steps of:
  storing an initial maximum impedance value;
  storing a minimum impedance value;
  determining a threshold impedance value between said initial maximum impedance value and said minimum impedance value;
  comparing a measured impedance value to said threshold impedance value; and
  generating a control signal to stop the application of RF energy to said tissue upon said measured impedance value exceeding said threshold impedance value.

* * * * *